US00PP37510P2

(12) United States Plant Patent
Nannes

(10) Patent No.: US PP37,510 P2
(45) Date of Patent: Jun. 30, 2026

(54) ***ECHEVERIA* PLANT NAMED 'BINL-77120108'**

(50) Latin Name: ***Echeveria* spp.**
Varietal Denomination: BINL-77120108

(71) Applicant: Botanical Innovation B.V., Wageningen (NL)

(72) Inventor: Jacobus A.M. Nannes, Nairobi (KE)

(73) Assignee: Botanical Innovation B.V. (NL)

( * ) Notice: Subject to any disclaimer, the term of this patent is extended or adjusted under 35 U.S.C. 154(b) by 0 days.

(21) Appl. No.: 19/344,945

(22) Filed: Sep. 30, 2025

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Susan Mccormick Ewoldt

(57) ABSTRACT

A new and distinct cultivar of *Echeveria* plant named 'BINL-77120108' is disclosed, characterized by flattened rosettes. Leaf color is intense greyed-purple, red-purple and brown leaf on aspices and margins with a fresh green base. The new cultivar is an *Echeveria*, typically used as an ornamental plant.

2 Drawing Sheets

Figure 1:
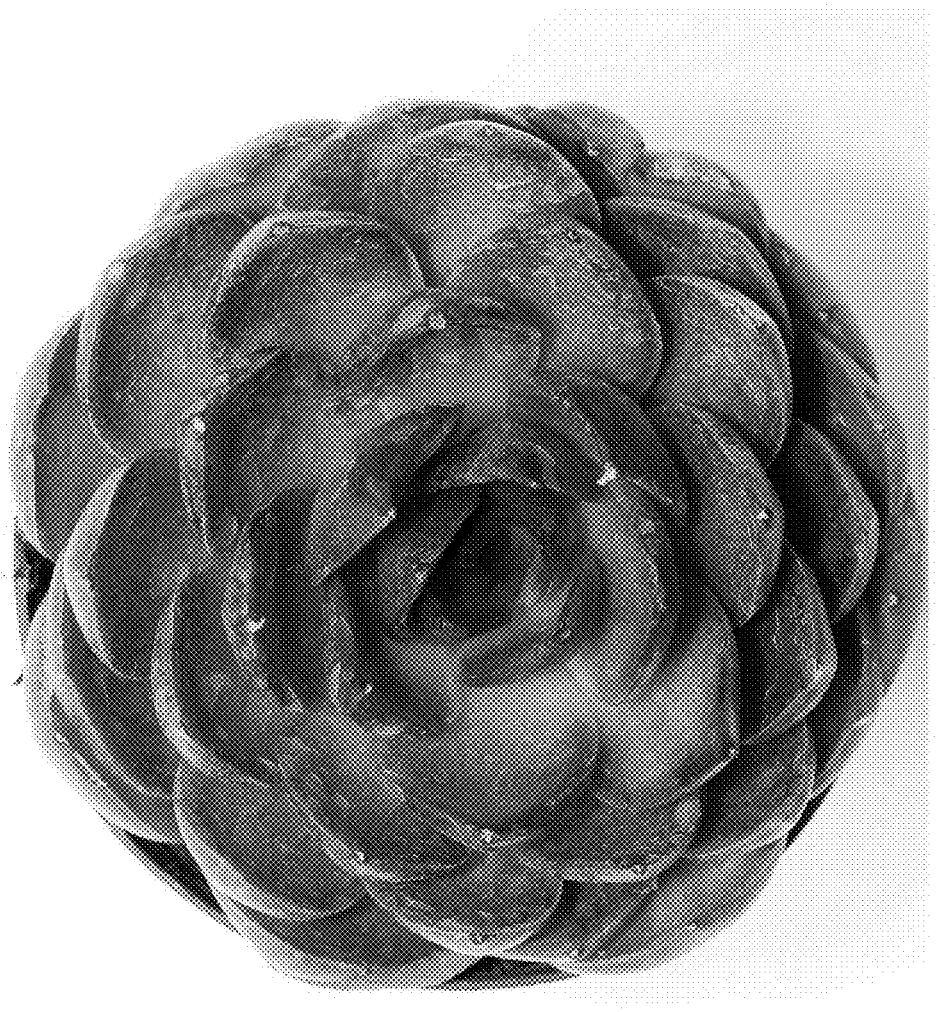

Latin name of the genus and species: *Echeveria* spp.
Cultivar denomination: 'BINL-77120108'.

BACKGROUND OF THE INVENTION

The new cultivar is a product of a planned breeding program to produce distinct *Echeveria* cultivars for ornamental purposes. The new cultivar is the result of a crossing made by the inventor in May of 2021. The seed parent is the unpatented *Echeveria* 'Christmas'. The pollen parent is the unpatented *Echeveria* 'Mont'. The new cultivar was selected by the inventor in August of 2022 at a nursery in Nairobi, Kenya.

Asexual reproduction of the new cultivar 'BINL-77120108' by terminal cuttings was first performed at the same nursery in Nairobi, Kenya in August of 2022, and has shown that the unique features of this cultivar are stable and reproduced true to type through successive generations.

SUMMARY OF THE INVENTION

The cultivar 'BINL-77120108' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BINL-77120108'. These characteristics in combination distinguish 'BINL-77120108' as a new and distinct *Echeveria* cultivar:

1. Intense greyed-purple, red-purple and brown leaf aspices and margins.
2. Thick leaves, hence not stretching easily or quickly.
3. Compact rosette-like plant-shape.
4. Strong greyed-purple coloration on the underside of the leaf.

PARENT COMPARISONS

Plants of the new cultivar 'BINL-77120108' are similar to plants of the female parent in most horticultural characteristics, however, plants of the new cultivar 'BINL-77120108' differ from in the following characteristics:

1. Leaf color of the new cultivar is intense red on the leaf-tips with a fresh green base. Leaf color of the seed parent is light green with a small/narrow red leaf-rim/edge at the top of the leaves.
2. Plants of the new cultivar have a less upright growth habit than plants of the seed parent.

Plants of the new cultivar 'BINL-77120108' are similar to plants of the male parent in most horticultural characteristics, however, plants of the new cultivar 'BINL-77120108' differ in the following characteristics:

1. Leaf color of the new cultivar is intense greyed-purple, red-purple and brown leaf on aspices and margins with a fresh green base. Leaf color of the pollen parent is more evenly colored, with younger leaves fully pinkish-green-red, older leaves turn to a more dull green color.
2. Leaves of the new cultivar are less rounded than leaves of the pollen parent.
3. Leaves of the new cultivar are slightly curved upwards, while leaves of the pollen parent are more flat.

COMMERCIAL COMPARISONS

Plants of the new cultivar 'BINL-77120108' are similar to plants of the unpatented commercial cultivar *Echeveria agavoides*, the species itself. However, plants of the new cultivar differ in the following characteristics:

1. Leaf color of the new cultivar is intense greyed-purple, red-purple and brown leaf on aspices and margins with a fresh green base. Leaf color of this comparator is light green with a small/narrow red-brown leaf-rim at the top of the leaf.

Plants of the new cultivar 'BINL-77120108' are similar to plants of the commercial cultivar *Echeveria* 'Spotlight', unpatented. However, plants of the new cultivar differ in the following characteristics:

1. Leaf color of the new cultivar is intense greyed-purple, red-purple and brown leaf on aspices and margins with a fresh green base. Leaf color of this comparator is green with red tips.

BRIEF DESCRIPTION OF THE PHOTOGRAPHS

The accompanying photograph in FIG. 1 illustrates in full color a top-down view of a typical plant of 'BINL-77120108' grown in a greenhouse. The plant is approximately 24 weeks of age.

Figure 2:
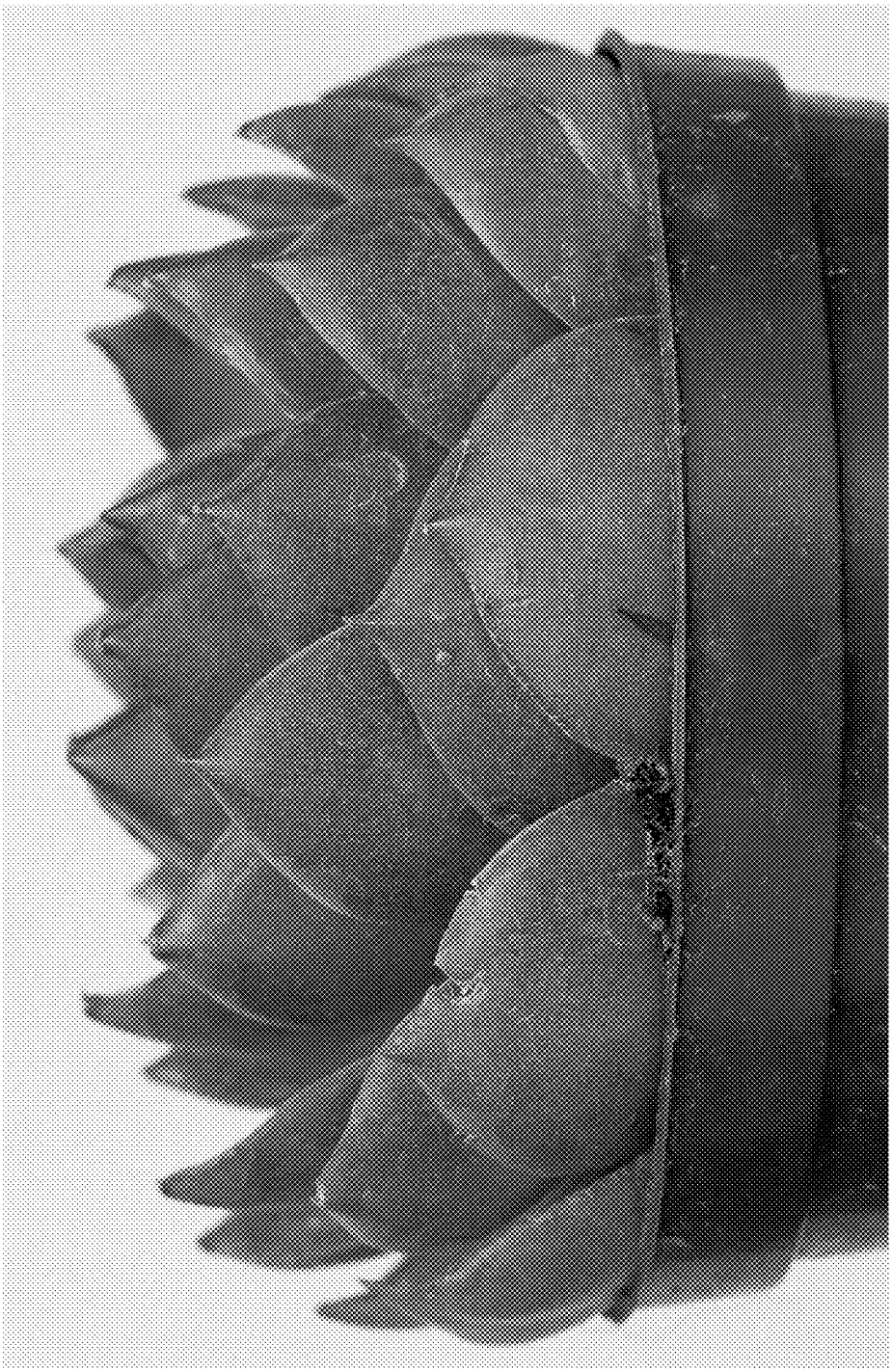

FIG. 2 is a side-view of the same plant.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'BINL-77120108' plants at 24 weeks of age, grown in a greenhouse in Nairobi, Kenya during August. The growing temperature ranged from 12° C. to 20° C. at night to 20° C. to 28° C. during the day. Measurements and numerical values represent averages of typical flowering types.

Botanical classification: *Echeveria* spp. 'BINL-77120108'.

PROPAGATION

Time to initiate roots: About 14 days in summer, 21 days in winter at approximately 20° C.

Time to produce rooted cutting: About 45 days in summer, 60 days in winter at approximately 20° C.

Description of roots: Thin, herbaceous, moderately dense, freely branching. White in color, not accurately measured with R.H.S. chart.

PLANT

Plant type: Tender succulent perennial.

Plant shape: Flattened (basal rosette).

Growth habit: Basal rosette of leaves.

Plant spread: Average 11.2 cm.

Height: Average 5.2 cm.

Age of plant described: Approximately 24 weeks.

Branching habit: Leaves in basal rosettes, no main stems or lateral stems present.

Pinching: Pinching not required.

FOLIAGE

Leaf:

*Arrangement*.—Single rosette.

*Quantity*.—Average 48 per rosette.

*Average length*.—6 cm.

*Average width*.—3.3 cm.

*Shape*.—Obovate, succulent.

*Aspect*.—Moderately to slightly concave, leaves in an average angle of 45° to horizontal (=0°).

*Apex*.—Abruptly acute to short apiculate.

*Base*.—Cuneate.

*Margin*.—Entire.

*Texture*.—Top surface: Glabrous, smooth. Bottom surface.—Glabrous, smooth.

*Pubescence*.—None; both sides glabrous.

*Luster, upper side*.—Slightly glossy.

*Luster, under side*.—Slightly to moderately glossy.

*Rugosity, upper side*.—Non-rugose.

*Rugosity, under side*.—Non-rugose.

*Color*.—Young foliage upper side: Lower half RHS Yellow-Green N148B, margin Purple 75D. Upper half Grey-Brown N199A, slightly tinged N199B, margin Red-Purple 59A flushed Greyed-Purple 185A, leaf apex Greyed-Purple 187A. Young foliage under side: RHS Yellow-Green N148C, strongly tinged Greyed-Purple 187B and 187C towards the top, margin Red-Purple 59A to Greyed-Purple 185A, leaf apex Greyed-Purple 187A. Mature foliage upper side: RHS Yellow-Green 147B, fading to 147C towards the base, upper half strongly tinged Greyed-Purple N186C with Brown 200A towards the distal end Leaf margined Greyed-Red 180A, fading to 180D towards base. Apex Greyed-Purple 187A. Mature foliage under side: RHS Yellow-Green; 146C and 147C, upper half strongly tinged Greyed-Purple 183A, N186C and 187A towards the top, margin Greyed-Red 181B. Apex Greyed-Purple 187A.

*Venation*.—Pattern: No veins visible.

*Other*.—Leaves succulent, average thickness: 8 mm.

OTHER CHARACTERISTICS

Flowers: Not observed to date.

Seeds and fruits: None observed to date.

Disease/pest resistance: Neither resistance nor susceptibility to normal diseases and pests of *Echeveria* has been observed.

Temperature tolerance: Tolerates temperatures up to 40° C. Hardy to USDA zones 11 to 13. Moderate tolerance to rain. High tolerance to wind.

What is claimed is:

1. A new and distinct cultivar of *Echeveria* plant named 'BINL-77120108' as herein illustrated and described.

* * * * *